United States Patent
Bruchmann et al.

(10) Patent No.: US 6,792,312 B2
(45) Date of Patent: Sep. 14, 2004

(54) CONNECTOR MODULE HAVING INTERNAL WELD PLATES

(75) Inventors: Richard A. Bruchmann, Andover, MN (US); George Patras, Plymouth, MN (US); Edwin Rivera, Ham Lake, MN (US)

(73) Assignee: Medtronic, Inc., Minneapolis, MN (US)

(*) Notice: Subject to any disclaimer, the term of this patent is extended or adjusted under 35 U.S.C. 154(b) by 313 days.

(21) Appl. No.: 09/947,614

(22) Filed: Sep. 6, 2001

(65) Prior Publication Data

US 2003/0045911 A1 Mar. 6, 2003

(51) Int. Cl.⁷ ............................................. A61N 1/375
(52) U.S. Cl. ...................................................... 607/37
(58) Field of Search ................................ 607/36–38, 1, 607/2

(56) References Cited

U.S. PATENT DOCUMENTS

| | | |
|---|---|---|
| 4,316,471 A | 2/1982 | Shipko et al. |
| 4,445,511 A | 5/1984 | Cowdery et al. |
| 4,934,366 A | 6/1990 | Truex et al. |
| 5,012,807 A | 5/1991 | Stutz, Jr. |
| 5,076,270 A | 12/1991 | Stutz, Jr. |
| 5,571,146 A * | 11/1996 | Jones et al. ............... 607/37 |
| 5,620,476 A | 4/1997 | Truex et al. |
| 5,632,274 A | 5/1997 | Quedens et al. |
| 5,899,930 A * | 5/1999 | Flynn et al. ............... 607/37 |
| 6,152,754 A | 11/2000 | Gerhardt et al. |
| 6,205,358 B1 | 3/2001 | Haeg et al. |

* cited by examiner

Primary Examiner—George R. Evanisko
(74) Attorney, Agent, or Firm—Elisabeth L. Belden; Girma Wolde-Michael

(57) ABSTRACT

An improved system and method for interconnecting an electrical device to a connector is provided. A connector assembly includes at least one connector block. The connector block may be of a type adapted to mechanically and electrically couple to an electrical lead, although any other type of connector for forming an electrical contact may be employed. The connector assembly further includes at least one weld plate. A conductor such as a wire is routed between the connector block and the weld plate and electrically coupled to both structures. The connector assembly is adapted to be fastened to a device housed within an enclosure, such as an implantable medical device residing within a can. A conductor extending from circuitry within the housing may be electrically coupled to the weld plate to thereby form an electrical connection between the circuitry and the connector block.

12 Claims, 6 Drawing Sheets

CONNECTOR MODULE HAVING INTERNAL WELD PLATES

FIELD

The invention relates to connector assemblies for electronic devices; and, more particularly, to component assemblies and processes for manufacturing implantable device connectors.

BACKGROUND

Implantable medical devices (IMDs), such as implantable cardioverter/defibrillators (ICDs) and pacemaker/cardioverter/defibrillators (PCDs), can detect and administer therapy for a variety of cardiac conditions. These conditions include ventricular fibrillation (VF), atrial fibrillation (AF), tachycardia, and bradycardia. IMDs typically include a housing that encloses a variety of internal components and isolates them from the implanted environment. Within the human body, for example, the housing must be sealed to prevent ingress of fluids which can cause the device to short circuit or corrode internal components, rending the IMD inoperable.

In many IMDs, integrated circuits, batteries, and other components are enclosed in hermetically sealed metallic enclosures known as "cans." In many systems, components within the IMD can are coupled electrically to components such as medical leads that are outside of the case. For example, one or more medical leads may be coupled to a connector module affixed to the outside of the can. The electrical connections between the connector module and the inside of the can are generally made by conductors extending between the connector and the IMD components.

By way of example, an ICD includes an internal battery, a charging capacitor, and electronic circuitry. The electronic circuitry is ordinarily coupled to pacing and diagnostic leads that are attached to a connector outside of the device housing for positioning within or near the heart. To protect internal components while permitting electrical connections with external components, the ICD includes a feedthrough assembly that preserves the environmental integrity of the device housing. The feedthrough assembly supports feedthrough pins that extend through the hermetically sealed can. These feedthrough pins are coupled to conductors such as wires. In prior art designs, these wires may be threaded through feedthrough apertures in the connector module. Then the wires are routed along an outside surface of a connector module so that they can be electrically coupled via a welding or soldering process to a respective connector block of the connector module.

Problems exist with the above-described manufacturing method. First, because the wires from the device must extend to a respective connector block of the connector assembly, the device wires must be relatively long. As a result, it is cumbersome to insert the device wires through the feedthrough of the connector block, and to then route the wires over the connector block surface.

Another problem with the prior art mechanism involves the use of jumper wires. If the original device wires are not long enough to extend to the desired connector block, jumper wires must be welded to the end of the wire to extend the length. Generally, this process involves a wire-to-wire, cross-welding process. This cross-welding is time-consuming and difficult. Moreover, the weld joints may exhibit undesirable mechanical and structural stresses that may affect the reliability, operation, and maintainability of the medical device. Finally, the weld joints have a tendency to buckle, which may cause a breach in the insulative adhesive material that is generally applied over the conductors to protect them from bodily fluids, leading to short circuits or other possible device failures.

Yet another problem associated with the above process involves the inability to ready the connector module for assembly on the device. Because the device wires are used as the conductors that couple the connector blocks with the internal device components, none of the welds may be completed prior to affixing the connector module to the can. As a result, much of the assembly work is performed in the last stages of device production, reducing the amount of parallelism that can be achieved during device assembly, and increasing the overall length of the assembly process. Additionally, performing the welding processes after the device is affixed to the connector is more cumbersome, increasing the complexity of the process.

Manufacturability is a significant concern in the design of implantable medical devices. As a result, efforts to simplify or reduce the complexity, cost, and time of the manufacturing process can directly impact the cost of the implantable medical device for patients. Accordingly, a more simple and cost-effective manufacturing process for use in the assembly of connector modules is needed.

SUMMARY

The invention is generally directed to interconnecting schemes for improved assembly of electronic devices, and implantable medical devices in particular. More specifically, a connector module incorporates internal weld plates that eliminate the need for extended-length device wires and cross-wire welds. As a result, the manufacturing process is greatly simplified, decreasing the unit cost of production.

One particular embodiment of the invention involves a device including at least one electrical component enclosed within a housing. The electrical component is electrically coupled to a device conductor such as a wire that extends outside of the housing. A connector assembly is positioned proximal the device, and may be affixed to the device with an adhesive and/or a fastening member. The connector assembly includes at least one connector block, such as may be adapted to mechanically and electrically couple to an electrical lead, although any other type of mechanism for making an electrical contact may be used as a connector block. The connector assembly further includes at least one weld plate. A conductor such as a wire is routed between the connector block and the weld plate and electrically coupled to both structures. The weld plate is further electrically coupled to the device conductor such that the electrical component is electrically coupled to the connector block.

According to one aspect of the invention, the connector assembly may include recessed channels such as wireways to maintain the conductors in a predetermined position along a surface of the connector assembly. At least a portion of one surface of the connector assembly may further be provided with an insulative layer such as an adhesive. This adhesive may be applied over one or more of the conductors, for example, to maintain the position of these components and provide an insulative, protective layer. The entire connector assembly may be coated with a material of this nature, if desired.

One example of the invention may be provided by an implantable medical device (IMD). The can of the IMD houses electronic circuitry. One or more device conductors coupled to the circuitry extend outside of the can. Affixed to the can is a connector assembly, which may include one or more connector blocks adapted to receive a respective connector member of a medical electrical lead. The connector assembly further includes one or more weld plates that may be molded within, or otherwise affixed, to a surface of the connector assembly. A conductor such as a wire extends between a given connector block and a weld plate, and is electrically coupled to each. A device conductor is further electrically coupled to a weld plate such that an electrical connection is made between the electronic circuitry and a given connector block.

Another embodiment is directed to a method of manufacturing an IMD system. An implantable medical device and a connector assembly are provided. The connector assembly includes at least one connector block and at least one weld plate. A conductor is arranged proximal to the connector assembly for electrically coupling a connector block with a weld plate. The connector assembly is then mounted to the IMD, and a device conductor extending from within the IMD is electrically coupled to the weld plate.

The system and method of the current invention simplifies the manufacturing of electronic devices such as IMDs by allowing most of the conductive traces to be attached prior to the coupling of the connector assembly with the device. This increases the parallelism possible in the manufacturing process. Additionally, the use of the weld plates allows the device conductors to be much shorter, since they do not need to extend directly to the connector blocks. This makes the assembly process less cumbersome. Moreover, the cross-weld interconnections formerly employed to couple jumper wires to the device conductors to extend their length may be eliminated. This eliminates a potential source of failure, as well as a time-consuming step in the assembly process. Finally, mechanical performance and reliability is also improved because of the reduced mechanical and structural stresses associated with the longer device conductors.

The above summary of the invention is not intended to describe every embodiment of the invention. The details of one or more embodiments of the invention are set forth in the accompanying drawings and the description below. Other features, objects, and advantages of the invention will be apparent from the description and drawings, and from the claims.

DETAILED DESCRIPTION

Figure 1:
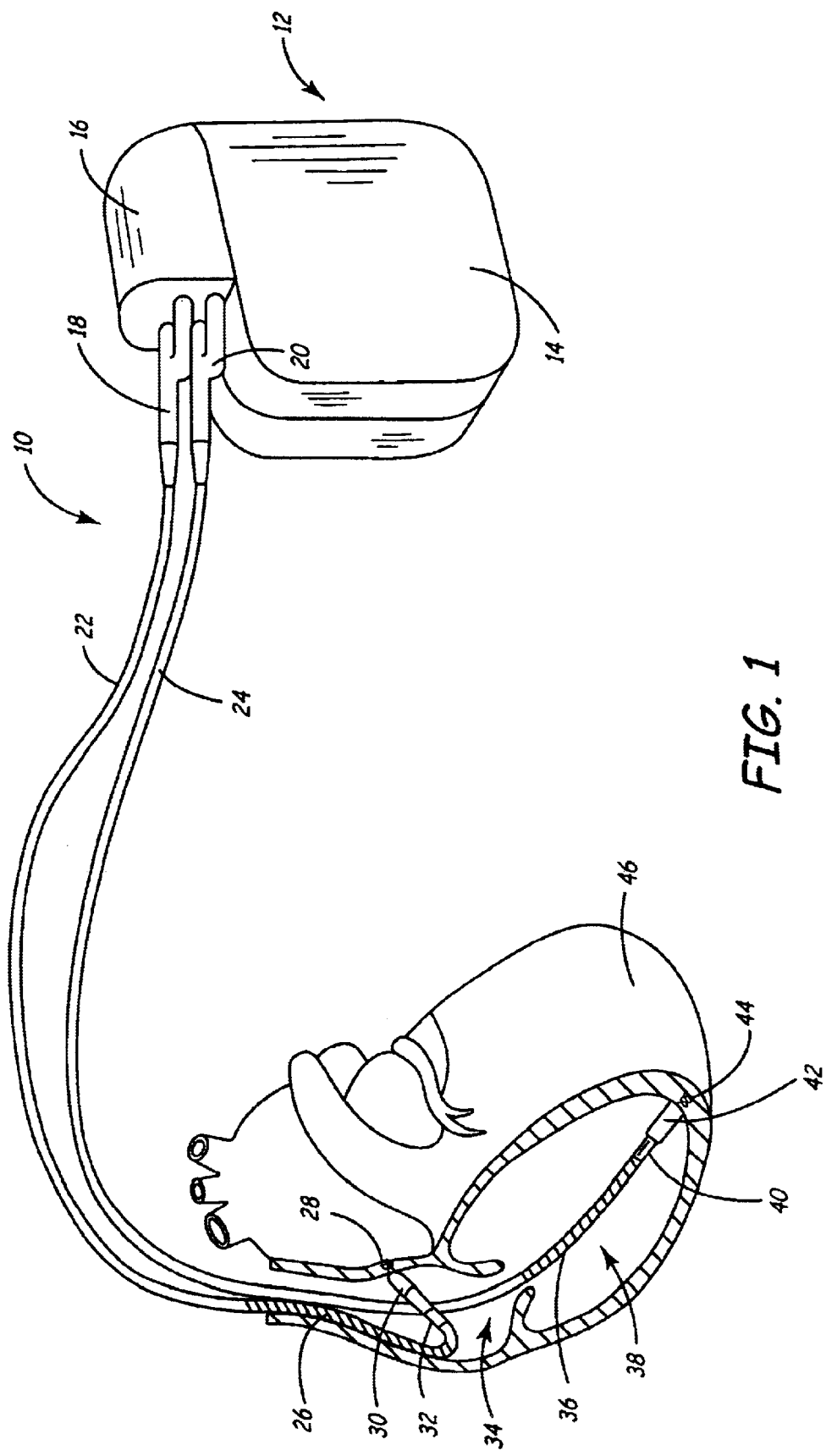
FIG. 1 illustrates an exemplary implantable medical device (IMD) system in which the present invention may be practiced.

FIG. 1 illustrates an exemplary implantable medical device (IMD) system 10 in which the present invention may be practiced. It will be understood that the present invention may be practiced with any other type of implantable device, including, but not limited to, pacemakers, cardioverter/defibrillators, and drug delivery devices.

IMD system 10 is shown in association with a human heart 46, and includes a pacemaker/cardioverter/defibrillator (PCD) 12 having a hermetically-sealed housing 14 and a connector assembly 16. Exemplary IMD system 10 comprises a ventricular lead, which includes an elongated insulated lead body 24. In one embodiment, the lead may carry three concentric coiled conductors separated from one another by tubular insulative sheaths, although many other lead configurations may be used within the system. The distal end of the ventricular lead is deployed in right ventricle 38. Located adjacent the distal end of the ventricular lead are a ring electrode 40, an extendable helix electrode 44 that may be mounted retractably within an insulative electrode head 42, and an elongated defibrillation coil electrode 36. Defibrillation electrode 36 may be fabricated from many materials, such as platinum or platinum alloy. Each of the electrodes is coupled to one of the coiled conductors within lead body 24.

Electrodes 40 and 44 are employed for cardiac pacing and for sensing ventricular depolarizations. Accordingly, electrodes 40 and 44 serve as sensors for a ventricular electrocardiogram (V-EGM). At the proximal end of the ventricular lead is a bifurcated connector 20 that carries three electrical connectors, each coupled to one of the coiled conductors.

The atrial/superior vena cava (SVC) lead includes an elongated insulated lead body 22 that may carry three concentric coiled conductors separated from one another by tubular insulative sheaths in a manner similar to that discussed above. The distal end of the atrial/SVC lead is deployed in right atrium 34. Located adjacent the distal end of the atrial/SVC lead are shown a ring electrode 32 and an extendable helix electrode 28, which may be mounted retractably within an insulative electrode head 30. Any other lead, fixation mechanism, and/or electrode configuration known in the art may alternatively be used with the current invention, and those shown are exemplary only.

Each of the electrodes may be coupled to one of the coiled conductors within lead body 22. Electrodes 28 and 32 are employed for atrial pacing and for sensing atrial depolarizations. Accordingly, electrodes 28 and 32 serve as sensors for an atrial electrocardiogram (A-EGM).

An elongated coil electrode 26 is provided proximal to electrode 32 and coupled to the third conductor within lead body 22. Electrode 26 may be 10 cm or more in length and configured to extend from the SVC toward the tricuspid valve. At the proximal end of the lead is a bifurcated connector 18 that carries three electrical connectors, each coupled to one of the coiled conductors.

In one embodiment, housing 14 of PCD 12 may be utilized as a can electrode. For example, all, or a selected uninsulated portion, of the housing 14 may serve as a subcutaneous defibrillation electrode, used to defibrillate either the atria or ventricles. Alternatively, housing 14 may be provided with an insulative coating, which may be formed of such materials as parylene or silicone rubber. This type of coating may be employed, for example, in some unipolar cardiac pacemakers.

Implantable PCD 12 is shown with lead connector assemblies 18 and 20 of leads 22 and 24, respectively, inserted into receptacles in connector assembly 16. These receptacles are electrically coupled to conductors extending from within the PCD housing via weld plates (not shown in FIG. 1) provided on the connector assembly 16. Use of these weld plates reduces manufacturing costs and provides a superior weld, as will be discussed in detail below.

Figure 2:
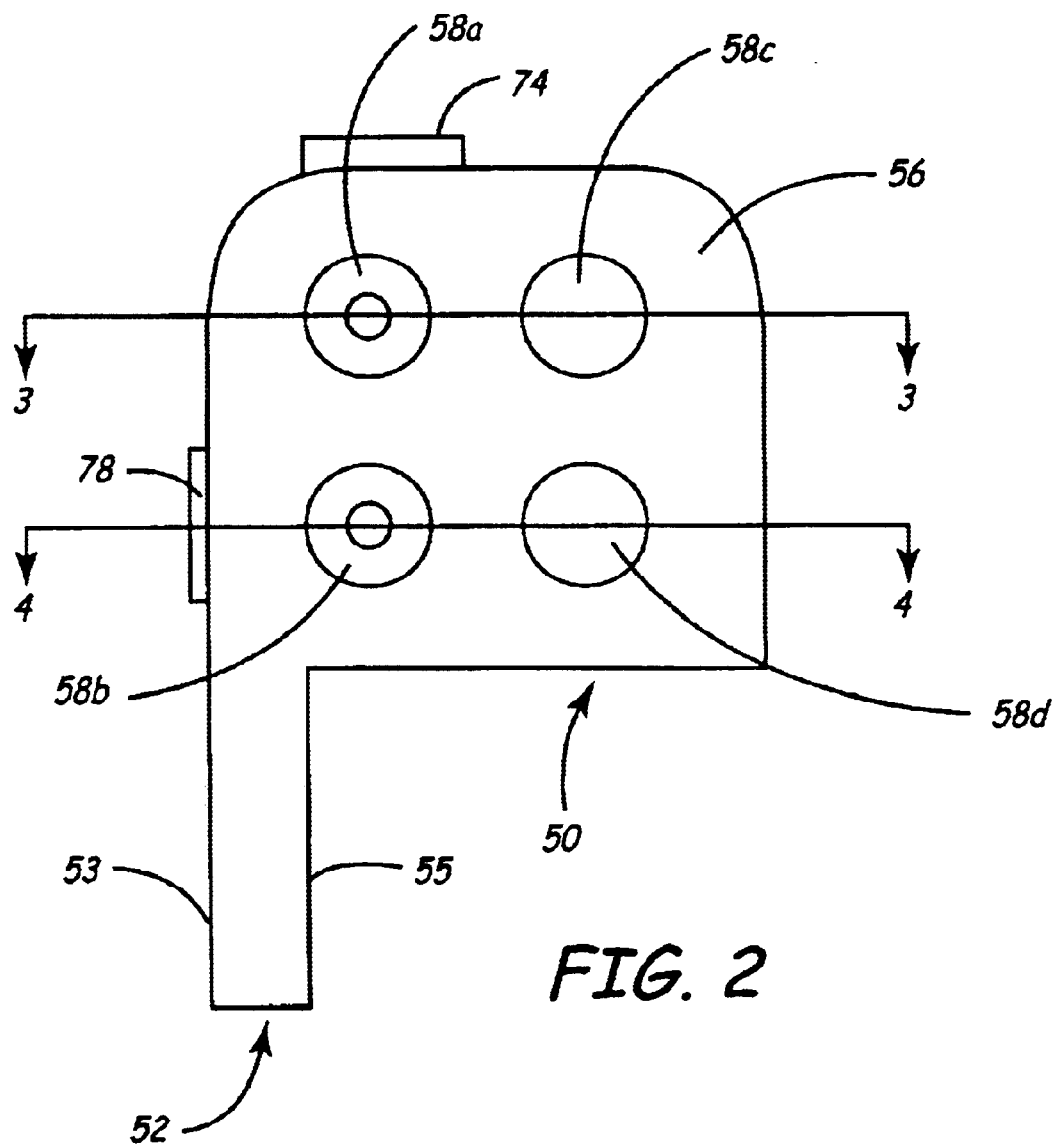
FIG. 2 is an end view of an exemplary connector assembly.

FIG. 2 is an end view of connector assembly 16 illustrating four receptacles 58a–58d extending into the connector assembly from front surface 56. The connector assembly includes a core member 17 that may be formed of a polymer such as polyurethane. The core member may be formed by a molding, machining, or any other process known in the art. The core member 17 includes receptacles 58a and 58b, which are shown as IS-1 standard connectors in FIG. 2. Similarly, core member includes receptacles 58c and 58d that may be isolated with DF-1 standard connectors, although it will be understood that any non-standard or standard connectors may be used within the scope of the current invention. These receptacles receive the connector assemblies 18 and 20 of leads 22 and 24, respectively, as shown in FIG. 1. The core member 17 further includes a bottom surface 50 that is adapted to mate with housing 14 of PCD 12.

FIG. 2 further illustrates flange 52 (not visible in FIG. 1). This flange includes an outer surface 53 and an inner surface 55. Inner surface 55 is adapted to mate with housing 14 of PCD 14. Outer surface 53 includes novel weld plates (not shown in this view) to be discussed further below. Grommets 74 and 78 may be included to provide a fluid-tight seal over various openings in the connector assembly, as described below.

Figure 3:
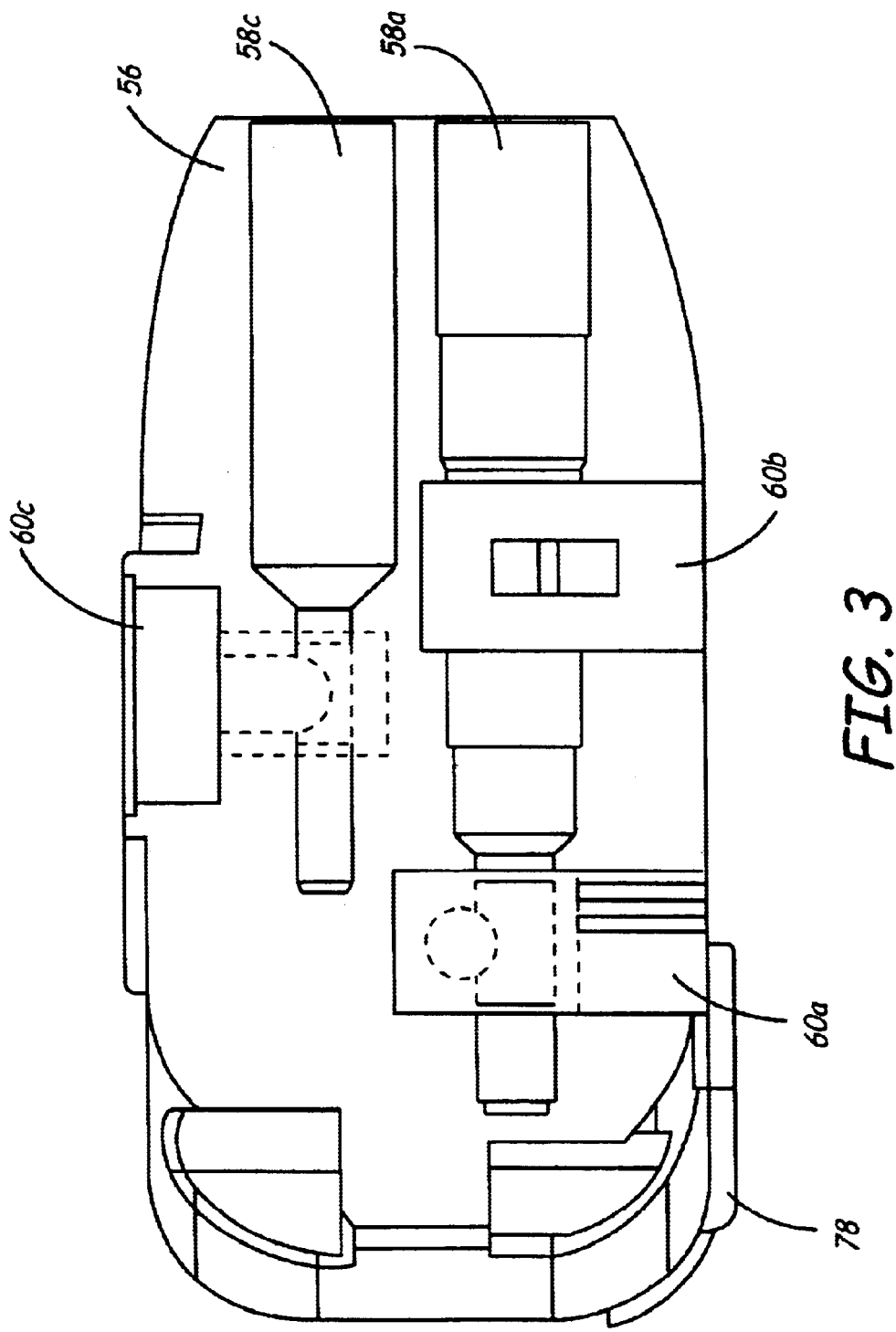
FIG. 3 is a cross-sectional view of the connector assembly along line 3—3 of FIG. 2.

FIG. 3 is a cross-sectional view of connector assembly 16 along line 3—3 of FIG. 2. This view shows receptacles 58a and 58c (FIG. 2) adapted to receive connector assembly 18. Connector blocks 60a and 60b are adapted to electrically and mechanically couple to a first pin and a ring connector of connector assembly 18, respectively. Similarly, connector block 60c is adapted to couple to a second pin connector of connector assembly 18. It will be appreciated that connector assembly 16 could be configured without connector block 60b if connector assembly 18 did not include a ring connector. Alternatively, an additional connector block could be provided to couple to an additional ring connector. Fewer connector blocks could be included, as would be the cases if a high-voltage electrode were not needed. Other configurations are also within the scope of the current invention.

Figure 4:
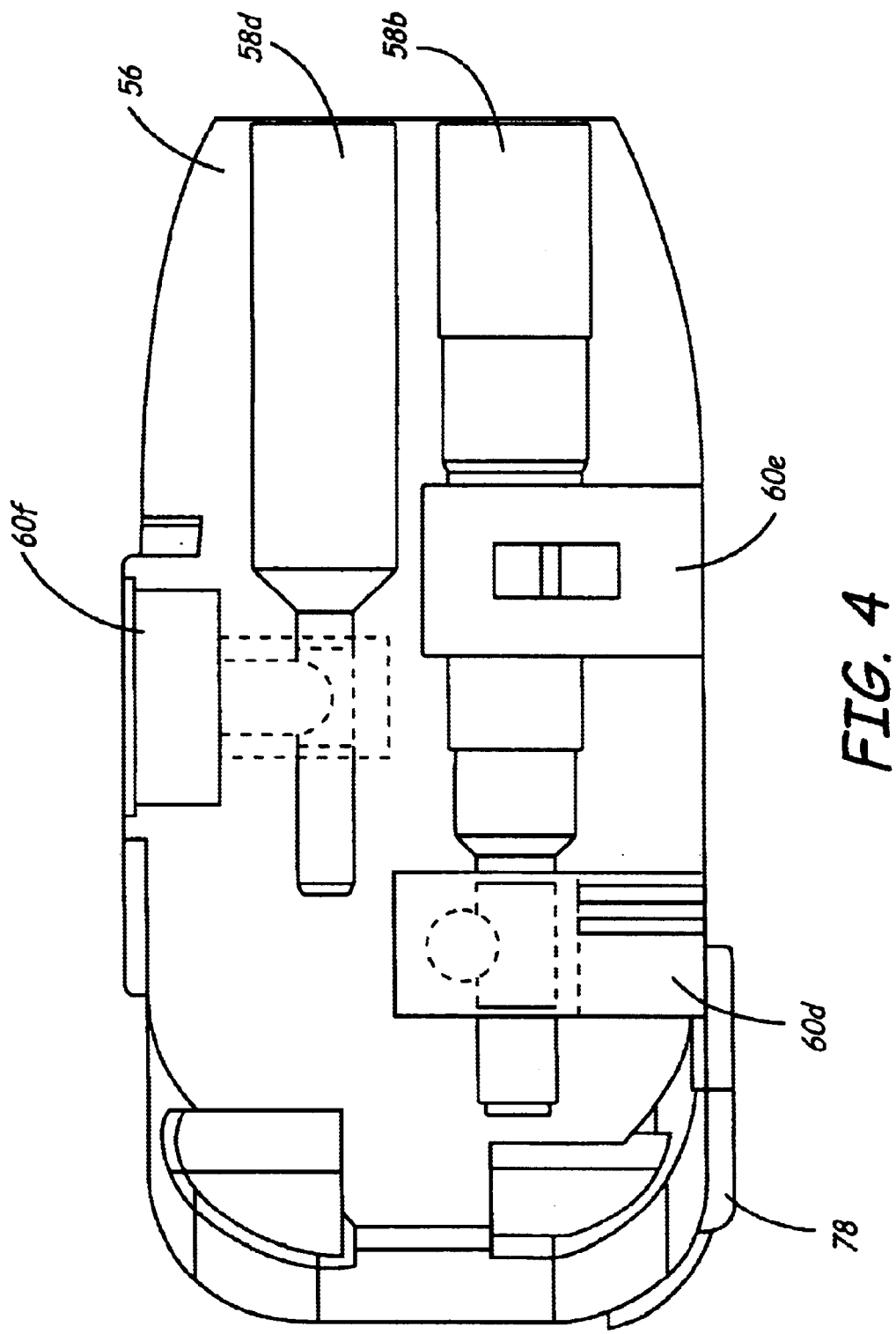
FIG. 4 is a cross-sectional view of the connector assembly along line 4—4 of FIG. 2.

FIG. 4 is a cross-sectional view of connector assembly 16 along line 4—4 of FIG. 2. This view is similar to that shown in FIG. 3. As discussed above in reference to FIG. 3, other configurations of the connector assembly 16 are within the scope of the current invention. For example, in a single-chamber pacing and/or ICD device, the additional connector blocks shown in FIG. 4 may not be necessary.

Figure 5:
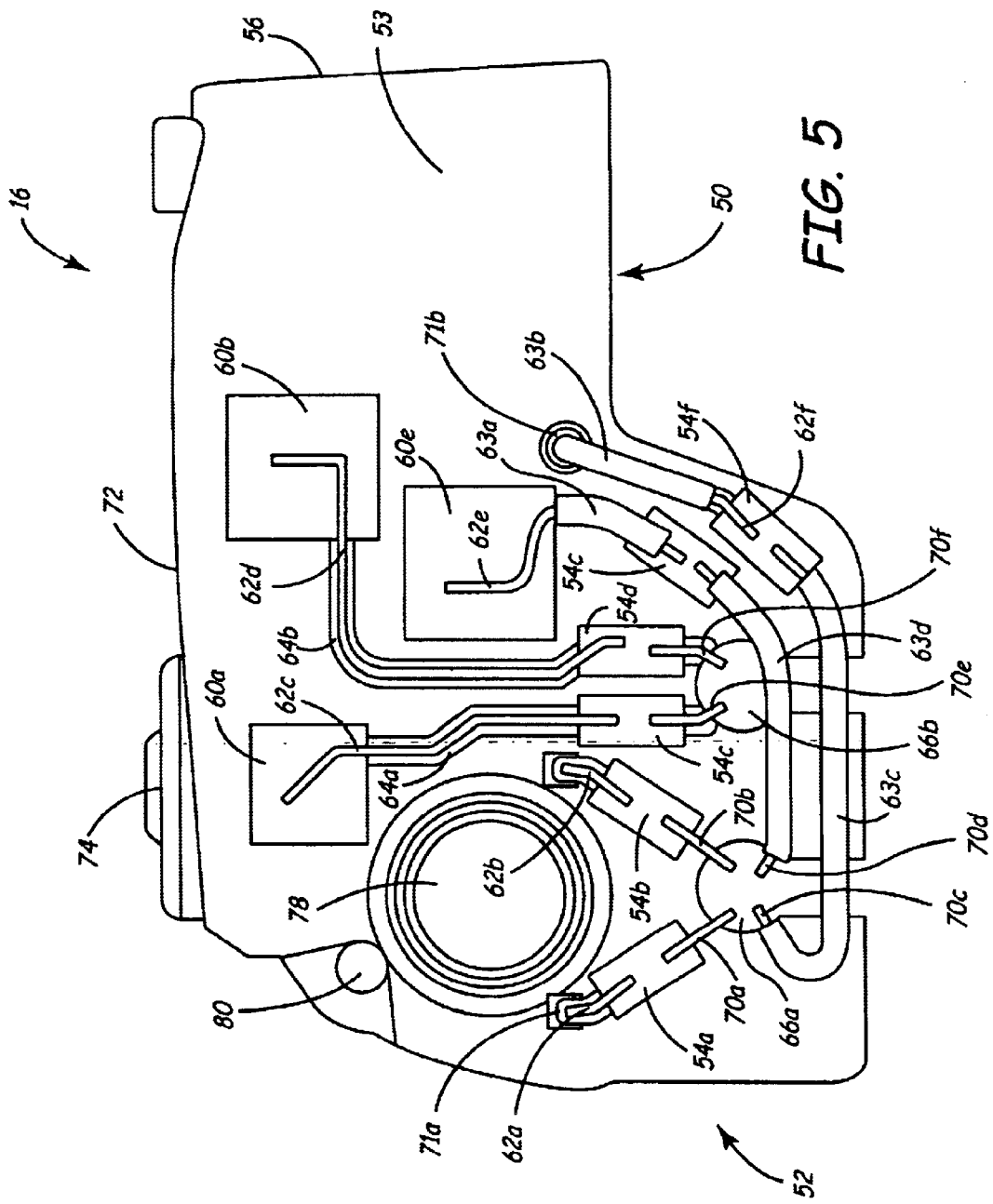
FIG. 5 illustrates an exemplary connector assembly including the novel weld plates of the current invention.

FIG. 5 illustrates surface 53 of connector assembly 16. During the assembly process, connector blocks 60a through 60f may be fitted into receptacles of the molded connector assembly 16 such that conductive surfaces are left exposed. Alternatively, if an overmold process were used, these components could be molded into the connector assembly, leaving one surface exposes. FIG. 5 illustrates connector blocks 60a, 60b, and 60e, with connector blocks (FIGS. 2–4) 60c, 60d, and 60f being visible from the opposite side of connector assembly 16.

In prior art designs, connector blocks could be directly coupled to conductors extending from an implantable device through a feedthrough in the connector assembly. These device conductors were routed along surfaces of the connector assembly and soldered or welded to the connector blocks. In some instances, the conductors were not long enough and jumper wires were required to extend the length and make the appropriate electrical connection. In either instance, welding and/or soldering of these conductors to the feedthrough blocks could not be performed until after the connector assembly 16 was coupled to the PCD. Additionally, because the device conductors had to be long enough to extend to the connector blocks, the handling, routing, and welding of these conductors was cumbersome. This made the manufacturing process time-consuming. Moreover, the conductors were more likely to become detached from the connector block, making device failure more likely. Finally, the cross-weld process generally used to mechanically and electrically couple a jumper wire to the device wire is time-consuming, and the resulting weld joint is prone to failures.

The current design simplifies the process by providing weld plates such as weld plates 54a–54f. These plates, which are formed of conductive material such as stainless steel, tantalum, or any other conductive material, may be adhesively affixed to the surface of the connector block, or may be molded into the connector block using an overmold process that leaves one surface of the weld plate exposed. These weld plates may be electrically coupled to the various connector blocks via conductive traces or wires. These conductors are shown in FIG. 5 as wires 62a through 62f, respectively. For example, connector blocks 60a, 60b, and 60e are shown mechanically and electrically coupled to weld plates 54c, 54d, and 54e, respectively, via wires 62c, 62d, and 62e, respectively. These wires may be welded in place prior to the connector assembly being affixed to the PCD, greatly simplifying the assembly process. This allows the connector assembly to be virtually device-ready so that the time to complete the final assembly process is greatly reduced. This increases the amount of parallelism that is possible within the assembly process, since much of the connector and device assembly can occur simultaneously.

Wires 54a–54f may be further held in place by wire ways, which are recessed channels formed in the molded surface of the connector assembly. For example, wire ways 64a and 64b are shown retaining wires 62c and 62d, respectively.

It may be noted from FIG. 5 that some of the wires 62 extend into receptacles molded into the connector assembly 16. For example, a first end of wire 62a is coupled to weld plate 54a, with the wire extending into receptacle 71a. Although not shown in FIG. 5, wire 62a is electrically coupled in this embodiment to connector block 60c (FIG. 3) which is inserted into a receptacle on the opposite surface of connector assembly 16. Likewise, wire 62b couples to weld plate 54b, and may be coupled to connector block 60d (FIG. 4), which is located behind grommet 78. Finally, wire 62f is shown coupled to weld plate 54f, and extends into receptacle 71b to couple to connector block 60f (FIG. 4). In this manner, all connector blocks are electrically coupled to a respective weld plate.

Any time after the connector assembly 16 is prepared in the manner described above, it may be attached to an implantable device such as PCD 12 (FIG. 1). For example, connector assembly 16 may be mounted on housing 14 of PCD 12 using fastening devices and/or adhesives such that surfaces 50 and 55 contact the housing 14. When the PCD is being attached to the connector assembly, external conductors coupled to the PCD are fed through feedthrough apertures such as feedthroughs 66a and 66b. These external conductors, which extend through housing 14 to internal circuitry within PCD 12, can be relatively short as compared to prior art designs because they need only extend to a respective weld plate instead of to a respective connector block. This makes the external conductors easier to handle.

In FIG. 5, device conductors 70a through 70d are shown extending through feedthrough 66a and coupling to a respective one of weld plates 54a, 54b, 54f, and 54e. Similarly, device conductors 70e and 70f are shown extending through feedthrough 66b and coupling to weld plates 54c and 54d, respectively. In one embodiment, wire ways or tubing such as tubes 63c and 63d may be provided to guide the device conductors and add stability to the completed assembly in a manner similar to that discussed above.

As may be noted in FIG. 5, some of the wires such as 62e, 62f, 70c, and 70d include an insulative coating shown as 63a–63d, respectively. This insulates the conductors to minimize the chance of electrical shorts. Additional insulation may be provided by applying a coating of medical adhesive to the external surfaces of the assembled device after the device conductors have been electrically coupled to the weld plates.

Many additional features may be provided by connector assembly 16 within the scope of the present invention. For example, in one embodiment, grommets 78 and 74 provide fluid-tight seals over receptacles that are adapted to receive a tool such as a screw driver. For example, grommet 74 may be provided to furnish a seal over a receptacle adapted to receive a tool that tightens a set-screw of connector block 60a. This allows connector assembly 18 of lead 22 to be fastened in position during an implant procedure. Similarly, grommet 78 may provide access to connector block 60d (FIG. 4) for a similar purpose.

Many alternative embodiments of the current invention are possible. For example, conductive traces may be utilized rather than wires 62a–62f. Additionally, more or fewer connector blocks 60 in alternative spatial configurations may be provided within the scope of the current invention. Any type of connector block may be utilized. The electrical couplings may be created using any type of soldering, welding, or other process known in the art for forming an electrical connection. In another embodiment, some of the device conductors 70 could be left longer so that they may be coupled directly to a connector block 60 without use of the weld plates, if desired. If desired, one or more of the device conductors could be coupled to jumper wires, although this is not preferred for reasons discussed above.

In one embodiment, a parallel gap weld is used to create the electrical couplings to the weld plates. This process allows all of the welds to be made in the same welding plane, rather than in multiple welding planes as is required in a cross-welding process. Moreover, maintaining the weld joints and all conductors substantially within a single plane along the surface of the device simplifies the process of applying the adhesive.

Figure 6:
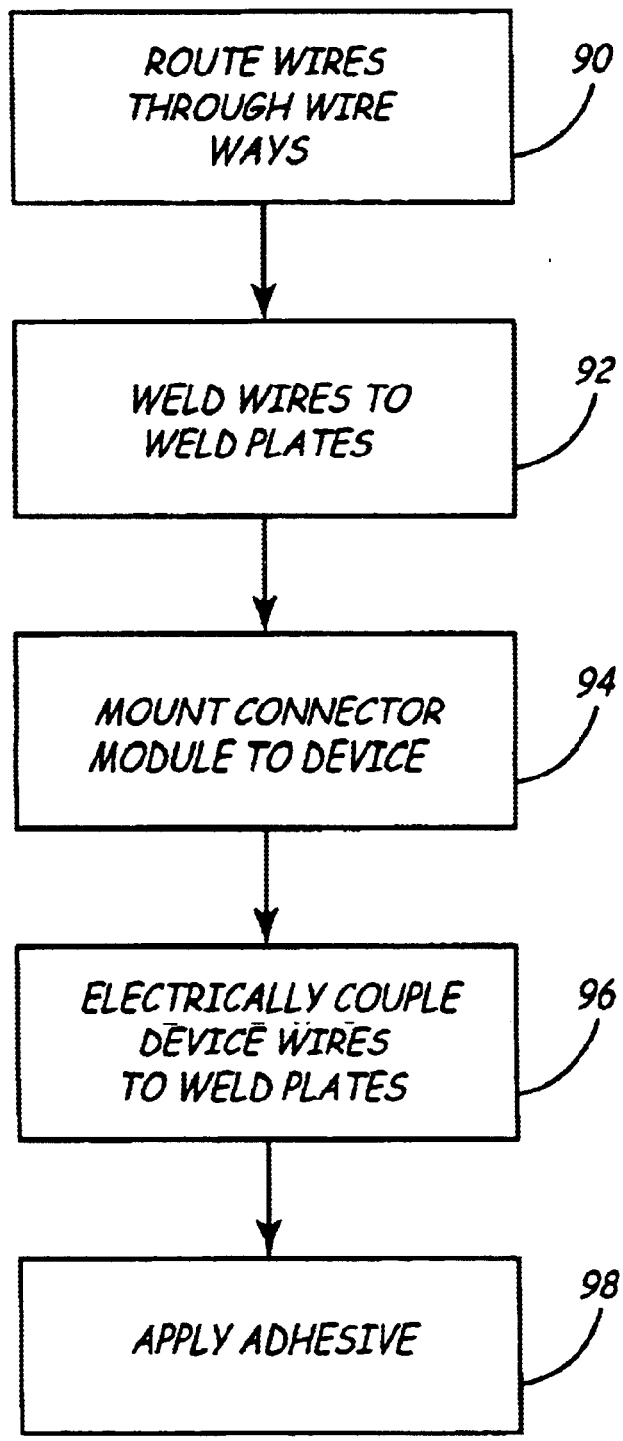
FIG. 6 is a flow diagram depicting an example process for manufacturing an implantable medical device according to the principles of the current invention.

FIG. 6 is a flow diagram depicting an example process for manufacturing an implantable medical device, such as PCD 12 of FIG. 1, according to the principles of the invention. Wires 62a–62f are routed (90) from electrical contacts such as the connector blocks 60 to the appropriate weld plates 54a–54f. Wireways may be provided to retain the wires in position during this process. Next, these wires are welded or otherwise electrically coupled to a respective weld plate to form an electrical connection with the associated connector block (92). Connector assembly 16 may then mounted to PCD 12 and secured, for example, using screws (94).

After mounting a connector assembly to an implantable device, conductors extending from the device are guided through openings such as feedthroughs in the connector assembly 16. These device conductors are welded or otherwise electrically coupled to a weld plate (96). A protective overcoat of biocompatible adhesive may then be applied to cover the device conductors and the weld plates (98).

As noted above, use of the weld plates simplifies the manufacturing of an implantable device by allowing most of the conductive traces to be attached prior to the coupling of the connector assembly with the device. This increases the parallelism possible in the manufacturing process. Additionally, the use of the weld plates allows weld joints to be formed that have a lower profile and are less prone to failure as compared to cross-wire welds. Finally, mechanical performance and reliability may be improved because of the reduced mechanical and structural stresses associated with the longer device conductors. This increases reliability due to the decreased likelihood of short circuits attributable to wires protruding through the adhesive or otherwise being exposed. These benefits result in an improvement in the overall efficiency and reliability of the manufacturing process.

Various embodiments of the invention have been described, although other embodiments are within the scope of the invention. For example, although in most embodiments, a one-to-one correspondence will exist between a connector block and a weld plate, this need not be the case. Multiple connector blocks may be electrically coupled to a single weld plate and vice versa, where desired. Moreover, it will be noted that although connector blocks are described herein as being adapted to couple to a lead, as may be accomplished using a multi-beam connector (MBC) for example, this is not necessarily the case. The connector blocks may take the form of any connector, coupling device, fastener or the like adapted to form an electrical connection with another component or device. Moreover, the conductors may take the form of conductive traces or any other type of conductive material instead of wires. Additionally, although some of the above-described embodiments relate to IMDs, it will be recognized that the invention may be applied to other electrical devices having connector assemblies similar to those discussed herein. These and other embodiments are within the scope of the following claims.

What is claimed is:

1. An implantable medical device for use with one or more implantable leads, the implantable medical device comprising:

a housing portion for housing electronic circuitry, the housing portion including a feedthrough;

a connector assembly fixedly engaged with the housing portion and including one or more connector receptacles adapted to receive the one or more leads;

a plurality of connector blocks fixedly positioned within the connector assembly such that each forms a coupling for a one of the one or more leads within a one of the one or more connector receptacles;

a plurality of first conductors each including a first portion coupled to a one of the plurality of connector blocks and a second portion extending from the first portion;

a plurality of second conductors each including a first portion coupled to the electronic circuitry and a second portion extending from the first portion outward from the housing portion through the feedthrough;

a plurality of weld plates;

a plurality of first weld joints each formed between a one of the plurality of first conductor second portions and a one of the plurality of weld plates; and a plurality of second weld joints each formed between a one of the plurality of second conductor second portions and a one of the plurality of weld plates.

2. The device of claim 1, wherein each of the plurality of first conductor second portions is individually routed within the connector assembly to a one of the plurality of weld plates.

3. The device of claim 1, wherein;
the connector assembly further includes a top surface, a bottom surface and a sidewall extending from the top surface to the bottom surface; and
wherein the plurality of weld plates are mounted in the sidewall.

4. The device of claim 3, wherein the connector assembly further includes a conductor receptacle extending from the sidewall laterally into the connector assembly to route a one of the plurality of first conductor second portions from a one of the plurality of connector blocks to a one of the plurality of weld plates.

5. The device of claim 3, wherein the connector assembly sidewall further includes a channel for routing a one of the plurality of first conductor second portions from a one of the plurality of connector blocks to a one of the plurality of weld plates.

6. The device of claim 3, wherein:
the housing portion further includes a housing top portion, a housing bottom portion, and a housing side portion extending between the housing top portion and the housing bottom portion;
the connector assembly bottom surface as fixedly engaged against the housing top portion;
the connector assembly sidewall further includes a flange portion extending from the bottom surface of the connector assembly, the flange portion including an inner surface and an outer surface, the inner surface fixedly engaged against the housing side portion; and
the plurality of weld plates are mounted in the flange portion of the sidewall.

7. The device of claim 3, wherein a one or more of the plurality of weld plates is adhesively attached to the sidewall.

8. The device of claim 3, wherein a one or more of the plurality of weld plates is molded into the sidewall.

9. The device of claim 1, wherein the plurality of weld plates are positioned approximately coplanar.

10. The device of claim 9, wherein the plurality of first joints and the plurality of second joints are formed via parallel gap welding.

11. The device of claim 1, further comprising a tubing guide positioned about a one of the plurality of first conductor second portions.

12. The device of claim 1, further comprising a tubing guide positioned about a one of the plurality of second conductor second portions.

* * * * *